United States Patent [19]

Maria Van Soom

[11] Patent Number: 4,919,999
[45] Date of Patent: Apr. 24, 1990

[54] WELDABLE MICROPOROUS NON-WOVEN TAPE FOR MEDICAL APPLICATIONS

[75] Inventor: Petrus L. A. Maria Van Soom, Vosselaar, Belgium

[73] Assignee: Avery International Corporation, Pasadena, Calif.

[21] Appl. No.: 197,032

[22] Filed: May 20, 1988

[30] Foreign Application Priority Data

May 22, 1987 [NL] Netherlands ............ 8701228

[51] Int. Cl.$^5$ .............................. C09J 7/02
[52] U.S. Cl. .............................. 428/284; 428/296; 428/343; 428/352; 428/354; 428/421; 428/422
[58] Field of Search .............. 428/343, 352, 354, 284, 428/421, 422, 296

[56] References Cited

U.S. PATENT DOCUMENTS

| | | | |
|---|---|---|---|
| 4,636,427 | 1/1987 | Ohno et al. | 428/354 |
| 4,784,653 | 11/1988 | Bolton et al. | 428/354 |
| 4,844,973 | 7/1989 | Konishi et al. | 428/354 |

Primary Examiner—James J. Bell
Attorney, Agent, or Firm—Christie, Parker & Hale

[57] ABSTRACT

There is provided a porous tape useful as a stoma-bag tape formed of a woven or non-woven web having on one surface a porous pressure sensitive adhesive and providing at the opposed surface a thermoplastic material which is weldable to another thermoplastic film. The construction has a moisture vapor transmission rate of at least 150 g/m$^2$/24 hr at 37° C. and will withstand a hydrostatic column of a 0.9% NaCl-H$_2$O solution at 11.5 cm height for at least 20 seconds without leakage.

15 Claims, 1 Drawing Sheet

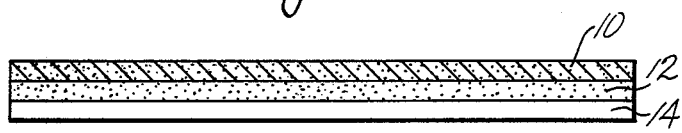
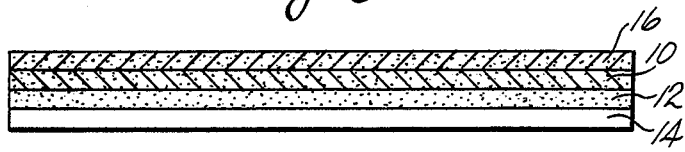
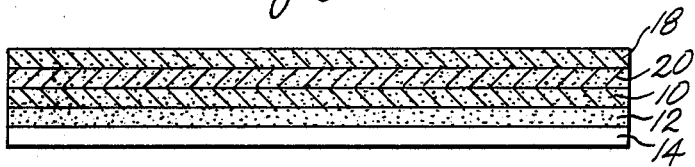

WELDABLE MICROPOROUS NON-WOVEN TAPE FOR MEDICAL APPLICATIONS

BACKGROUND OF THE INVENTION

The present invention relates to a microporous tape to be adhered to human skin by means of an adhesive layer harmless to the skin, providing the unique combination of both moisture-vapor permeability and hydrostatic-pressure resistance that, in effect, provides a liquid barrier. The tape is also weldable to a thermoplastic film. This product is highly suitable to be used as self-adhesive flange for stoma bags. Beside the use as a self-adhesive welding flange for stoma bags, the tape is also suitable for the use as surgical plaster. Due to its vapor permeability, no moist film will develop between the adhesive layer and the human skin which would result in a loss of adhesive qualities and an uncomfortable feeling for the person. In the use of the liquid barrier, mechanical qualities of the tape are maintained and a bacterial barrier is produced, so that the risk of exogenous bacterial infection to a plaster-covered wound is minimized.

Another application is the use of said tape adhered to human skin, including the optimal use of thermoplastic auxiliaries fused upon the non-adhered side such as for example an electrocardiogram electrode. The numerous kinds of commercially available stoma-bags for both colostomia- and ileostomia patients consist of a self-adhesive, flange which has as a function that the stoma bag can be attached to the stoma with a self-adhesive tape construction. Self-adhesive tapes are also commercially available, said tapes show a certain MVTR (moisture-vapor transmission rate), to allow constant breathing of the skin when covered with tape. However, this implies that an open construction is to be made which has a drawback that it is hardly or not moisture proof. In other words water from the outside contacting the tape, for example when the stoma patient with the stoma-bag adhered to the skin would take a shower or bath can penetrate tape and cause adhesive failure.

An internal market study of a number of European stoma bags' manufacturers showed that there is a demand for self-adhesive tape meeting the following requirements:
- non-irritating pressure-sensitive adhesive,
- moisture vapor permeable woven or non-woven tape,
- moisture repellent non-adhered side,
- non-adhered side fusible by means of heat, and/or high frequency radio waves to a thermoplastic film,
- strong, i.e., hard to tear, but flexible product.

Due to the fact that the thermoplastic film can be welded to the non-adhered side of the tape, the stoma-bags manufacturer is in a position to produce the stoma bag in a more efficient and economical way.

Microporosity and moisture vapor permeability can be measured in various ways and a possibility is to measure the amount of air expressed in milliliters per minute (ml/min) by a known surface at a certain pressure. However, the most relevant and practice-based test, is measurement of the MVTR (moisture vapor permeability rate) expressed in grams of water per meter square per 24 hours (g $H_2O/m^2/24$ hr.) at 37° C. The water-repellency may be measured by means of water retention in the web after its immersion. Another method to measure the water repellency is to measure the time up to leakage caused by a static liquid column of a specified height positioned on the tape.

SUMMARY OF THE INVENTION

According to the present invention there is provided a weldable microporous tape construction suitable for use with stoma-bags and other applications. In its basic form the microporous tape consists of a web of woven or non-woven fibers coated with an emulsion of a thermoplastic polymer and a water repellent agent such as a fluorocarbon to which is there applied a microporous pressure sensitive adhesive. The construction is formulated in a manner in that will have a moisture vapor transmission rate independent of direction of moisture vapor transmission of at least 150 grams per meter square for 24 hours at 37. but at the same time will withstand a hydrostatic head of a 0.9% $NaCl-H_2O$ solution of 11.5 centimeters height for at least 20 seconds without leakage. In this way moisture can be transmitted readily away from the body through the adhesive and the web while at the same time the web will be sufficient water resistant to prevent water attack and loosening of the adhesive. The thermoplastic selected is one which is weldable by heat, radio frequency waves, ultrasonic techniques and the like to a plastic surface as would be used in the construction of a stoma-bag.

In an alternate construction, the web layer is coated with a weldable thermoplastic material leaving still a microporous surface which will transmit the required amount of moisture from the skin and at the same time resist liquid water penetration.

In yet a third construction, a porous film is applied with or without an adhesive to the web with the porosity being inherently in the film or later developed by other means. In all constructions there may be provided a silicone release liner to protect the adhesive until use.

The feature of the invention is the balance of the moisture vapor permeability and on the liquid barrier which look contradictory. A microporous construction will show a high MVTR, but otherwise will have quite a low water barrier. A high water barrier can be achieved by sealing the non-woven completely by means of a film, but then only a very low, if any, MVTR will be achieved.

By treating the web with a water-repellent agent and subsequently coating the web with a microporous adhesive, the unique combination of moisture vapor permeability and liquid barrier is achieved. When MVTR is plotted as a function of the liquid barrier a line is obtained which, dependent on the microporosity of the adhesive layer, the degree of water repellency which can be obtained via a plurality of techniques, and the density of the non-woven, will shift to the right to a limit as described below. By an appropriate selection of the applied materials it is also possible to prepare the non-adhering side of the tape for welding to a thermoplastic film.

BRIEF DESCRIPTION OF THE DRAWINGS

FIG. 1 illustrates the layers of one construction of the instant invention;

FIG. 2 illustrates the layers of yet another construction of the invention;

FIG. 3 illustrates the layers of yet a third construction of the invention.

DETAILED DESCRIPTION

The invention relates to a laminated product characterized in that the product comprises a porous, woven or non-woven web of paper, synthetic or natural fibers to which an adhesive coating layer is applied and the product is coated and/or impregnated with a thermoplastic material and a water repellant agent in such a way that it has a moisture vapor transmission rate independent of the direction of at least 150 g/m²/24 hr. at 37° C. and at the same time will withstand a hydrostatic column of a 0.9% NaCl-H₂O solution of 11.5 cm height for at least 20 seconds without leakage, said product optionally being covered by a protective release liner.

A preferred product is characterized in that the product has either a liquid barrier between 20 and 350 seconds measured With a 11.5 cm static liquid column of a 0.9% NaCl-H₂O solution and a moisture-vapor permeability between 150 and 3000 g/m²/24 hr. at 37° C. or a liquid barrier between 350 and 1000 seconds measured with a 11.5 cm static liquid column of a 0.9% NaCl-H₂O solution and a moisture permeability between 150 and 1400 g/m²/24 hr. at 37° C.

The non-adhered side of the product is weldable to a synthetic film by means of heat, high frequency radio waves, ultrasonic techniques and the like.

Among the thermoplastic material there may be mentioned polymers containing vinyl acetate such as polyvinyl acetate, ethylene vinyl acetate copolymers, and the like, vinyl chloride polymers, and the like, as well as mixtures thereof.

It is presently preferred to use an ethylene vinyl acetate copolymer manufactured and sold Wacker Chemie and under the trade name Vinnapas. It is applied to the web as an emulsion with a hydrophobic fluorocarbon manufactured by Asaki Chemical and sold under the trade name Asaki Guard 710. Other fluorocarbons and silicon containing compounds such as polysilanes may also be used.

The adhesive is to be moisture permeable and non-irritating to the skin. A suitable adhesive is a polyacrylate pressure sensitive adhesive manufactured by National Starch and Chemical and sold in Europe under the designation Duro-Tak 280-2516.

The present invention can be achieved in various ways discussed here below in greater detail.

With reference to FIG. 1, a first construction comprises impregnation, spraying or foam-coating of a non-woven 10 with an emulsion consisting of a fluorocarbon providing the water-repellency to the total construction and a polyvinyl chloride, polyvinyl acetate or the like to make it possible in the final application to weld thermally by means of heat or high frequency radio waves to a thermoplastic coextruded copolymer films such as ethyl vinylacetate-polyethylene or film consisting of polyvinylidene chloride-polyethylene to the treated non-woven. The preferred non-woven is a polyamide. In a second step a microporous pressure-sensitive adhesive layer 12 harmless to the skin is attached to the non-woven by means of a direct or transfer coating.

Producing a microporous adhesive can be done chemically by starting a chemical reaction for gas-producing after applying the adhesive layer to the support. A physical way includes mixing air or an inert gas in the adhesive prior to or during the coating of the support with the adhesive layer. In both cases micropores are produced in the adhesive layer to provide the porous character. The whole construction may optionally be coated with a removable silicon release lines 14 dependent on the final use and/or used coating technique.

MVTR values of the material may vary of about 1000 to 3000 g/m²/24 hr. at 37° C. and a water repellency measured with a 11.5 cm high liquid column of a 0.9% NaCl-H₂O solution of some seconds to minutes dependent on the thickness of the adhesive layer, the absolute adhesive area, i.e., microporosity percentage and the density of the non-woven. A typical example is the impregnation of a 35 g/m² 100% polyamide spunlaid non-woven with the above mentioned emulsion comprising a fluorocarbon and polyvinyl acetate. Thereto a 30 g/m² microporous polyacrylate adhesive is applied by means of a transfer coating technique. The tape construction shows a MVTR of 2900 g/m²/24h at 37° C. and a water repellency of 180 sec.

As shown in FIG. 2, a second construction is the roller- or extrusion coating of a thermoplastic material, in this case ethylene vinyl acetate film 16 on a non-woven. However, this has to provide a non-closed (porous) film to be obtained by a correct temperature, in order to obtain penetration of the coating into the non-woven, to produce a non-closed film. Subsequently a microporous layer can be applied to the non-coated side of the non-woven as described above for FIG. 1. The water-repellency can be enhanced by treating the non-woven in a preceding step with a fluorocarbon as described in respect of the construction of FIG. 1 with or without a polymer.

An example of said method is applying a 25 g/m² hot melt ethylene vinyl acetate copolymer by means of a diecoating to a water-repellent 35 g/m² 100% polyamide spunlaid non-woven, thereafter applying a 30 g/m² microporous polyacrylate adhesive to the non-coated side with a transfer-coating technique. By means of this technique identical values can be obtained as described for the construction for FIG. 1. Here it is also possible depending on the final application to change the MVTR and/or water barrier dependent on the selection of the thickness of the adhesive layer, the absolute adhesive area, i.e., microporosity, the density of the non-woven fabric, the water-repellency of the non-woven fabric, and the thickness and/or degree of sealing of the ethylene vinyl acetate coating layer.

As shown in FIG. 3, a third construction is the application of a perforated thermoplastic film 18 to the non-woven. Application may take place by means of heat, and/or pressure-lamination or by adhering with layer 20. However, the adhesive medium should be a non-closed layer, because otherwise the result is a too closed construction with too low a MVTR. Therefore it is recommendable to apply the adhesive layer 20 in a grid pattern.

In a further step a microporous adhesive layer is also applied as described for FIG. 1. Optionally the liquid barrier may further be enhanced by using a water-repellent non-woven as also described in FIG. 1.

An example of the above described manner is heat laminating of a 25 micron, 60 mesh/100 microns (average) perforated polyethylene film on a water-repellent 35 g/m² 100% polyamide spun laid non-woven.

In a further step a 30 g/m² microporous polyacrylate adhesive layer is applied to the non-laminated side of the non-woven. Characterizing values are a MVTR of 2900 g/m²/24 hr. at 37° C. and a water-repellency of 180 sec. for 0.9% NaCl-H₂O solution at a column of 11.5 cm high.

An alternative method is heat lamination and/or pressure lamination, or by extrusion of a sealed thermoplastic film on the non-woven, and in a further step this laminate is physically microperforated with e.g. a needle roller, laser beam, or a high-pressure water jet. Subsequently a microporous adhesive layer optionally covered with a protective release liner is applied to said treated laminate.

What is claimed is:

1. A laminated product comprising a porous, woven or non-woven web of paper, synthetic or natural fibers, said web having on one surface thereof a porous pressure sensitive adhesive coating layer and said web providing at the surface opposed to the adhesive coating a thermoplastic material which is weldable to another thermoplastic material said laminated product having a moisture vapor transmission rate of at least 150 g/m$^2$/24 hr at 37° C. while withstanding a hydrostatic column of a 0.9% NaCl-H$_2$O solution of 11.5 cm height for at least 20 seconds without leakage.

2. A laminated product as claimed in claim 1, in which the laminated product withstands for between 20 and 350 seconds a 11.5 cm hydrostatic liquid column of a 0.9% NaCl-H$_2$O solution and the moisture-vapor transmission rate is between 150 and 3000 g/m$^2$/24 hr at 37° C.

3. A laminated product as claimed in claim 1 in which the laminated product withstands for between 350 and 1000 seconds 11.5 cm hydrostatic liquid column of a 0.9% NaCl-H$_2$O solution and the moisture transmission rate is between 150 and 1400 g/m$^2$/24 hr at 37° C.

4. A laminated product as claimed in claim 1 in which the thermoplastic material is weldable to another thermoplastic material by means of heat, high frequency radio waves or ultrasonic techniques.

5. A laminated product as claimed in claim 2 in which thermoplastic material is weldable to another thermoplastic material by means of heat, high frequency radio waves or ultrasonic techniques.

6. A laminated product as claimed in claim 3 in which thermoplastic material is weldable to another thermoplastic material by means of heat, high frequency radio waves or ultrasonic techniques.

7. A laminated product as claimed in claim 1 in which the thermoplastic material provided by the web comprises polymerized vinyl acetate.

8. A product as claimed in claim 1 in which the web contains a water repellant fluorocarbon.

9. A product as claimed in claim 7 in which the web contains a water repellant fluorocarbon.

10. A product as claimed in claim 1 in which the thermoplastic material is contained in the web.

11. A product as claimed in claim 9 in which the thermoplastic material is contained in the web.

12. A product claimed in claim 1 in which the thermoplastic material is coated on the web.

13. A product claimed in claim 9 in which the thermoplastic material is coated on the web.

14. A product as claimed in claim 1 in which the thermoplastic material is a porous film adhered by a porous adhesive to the web.

15. A product as claimed in claim 9 in which the thermoplastic material is a porous film adhered by a porous adhesive to the web.

* * * * *